(12) United States Patent
Kamrava (10) Patent No.: US 8,469,876 B2
(45) Date of Patent: Jun. 25, 2013

(54) ENDOSCOPIC DEVICES AND METHOD OF USE

(75) Inventor: Michael M. Kamrava, Los Angeles, CA (US)

(73) Assignee: Michael Levy, Beverly Hills, CA (US)

( * ) Notice: Subject to any disclaimer, the term of this patent is extended or adjusted under 35 U.S.C. 154(b) by 1984 days.

(21) Appl. No.: 10/725,623

(22) Filed: Dec. 1, 2003

(65) Prior Publication Data

US 2004/0122286 A1 Jun. 24, 2004

Related U.S. Application Data

(63) Continuation-in-part of application No. 10/080,177, filed on Feb. 19, 2002, which is a continuation-in-part of application No. 09/759,415, filed on Jan. 12, 2001, now Pat. No. 6,623,422.

(51) Int. Cl.
*A61B 17/43* (2006.01)
*A61D 7/00* (2006.01)

(52) U.S. Cl.
USPC .................................. 600/33; 600/34; 600/35

(58) Field of Classification Search
USPC ............................................... 600/33, 34, 35
See application file for complete search history.

(56) References Cited

U.S. PATENT DOCUMENTS

| | | | |
|---|---|---|---|
| 3,709,214 A | 1/1973 | Robertson | |
| 3,742,958 A | 7/1973 | Rundles | |
| 3,915,168 A | 10/1975 | Monestere, Jr. et al. | |
| 4,203,430 A | 5/1980 | Takahashi | |
| 4,474,576 A * | 10/1984 | Gobby | 604/176 |
| 4,490,139 A | 12/1984 | Huizenga et al. | |
| 4,534,339 A | 8/1985 | Collins et al. | |
| 4,689,040 A | 8/1987 | Thompson | |
| 4,779,612 A | 10/1988 | Kishi | |
| 4,836,189 A | 6/1989 | Allred, III et al. | |

(Continued)

FOREIGN PATENT DOCUMENTS

| | | |
|---|---|---|
| DE | 3702441 | 8/1988 |
| GB | 2118840 | 11/1983 |

(Continued)

OTHER PUBLICATIONS

Itskovitz-Eldor J, et al., "Assisted implantation: direct intraendometrial embryo transfer," Gynecol Obstet Invest, 1997; 43(2):73-5, Haifa, Israel.

(Continued)

*Primary Examiner* — Patricia Bianco
*Assistant Examiner* — Camtu Nguyen (57) ABSTRACT

A catheter including a shaft comprising a body with a proximal portion and a distal portion, the body defining an opening from the proximal portion to the distal portion, the distal portion having an end that is beveled in a first direction across an end opening, such that a length of the shaft to a first point on the end is a first length and a length of the shaft to a second point on the end is a second length longer than the first length. A method including placing at least one embryo near an open end of a catheter, inserting the open end of the catheter into an endometrial lining of a subject's uterus, using the catheter to open a flap of the endometrial lining, and transferring the at least one embryo from the catheter to the pocket site.

25 Claims, 9 Drawing Sheets

U.S. PATENT DOCUMENTS

| | | | |
|---|---|---|---|
| 4,846,785 A | | 7/1989 | Cassou et al. |
| 4,850,960 A | | 7/1989 | Grayzel |
| 4,863,423 A | | 9/1989 | Wallace |
| 4,890,602 A | | 1/1990 | Hake |
| 4,911,148 A | | 3/1990 | Sosnowski et al. |
| 4,997,419 A | | 3/1991 | Lakatos et al. |
| 5,002,535 A | | 3/1991 | Gross |
| 5,057,083 A | * | 10/1991 | Gellman ............... 604/164.1 |
| 5,167,645 A | | 12/1992 | Castillo |
| 5,195,979 A | | 3/1993 | Schinkel et al. |
| 5,199,417 A | | 4/1993 | Muller et al. |
| 5,217,466 A | | 6/1993 | Hasson |
| 5,325,845 A | | 7/1994 | Adair |
| 5,342,325 A | | 8/1994 | Lun et al. |
| 5,360,389 A | | 11/1994 | Chenette |
| 5,394,887 A | | 3/1995 | Haaga |
| 5,397,512 A | * | 3/1995 | Sloane et al. ............ 264/482 |
| 5,472,419 A | * | 12/1995 | Bacich ..................... 604/515 |
| 5,484,422 A | | 1/1996 | Sloane, Jr. et al. |
| 5,536,259 A | | 7/1996 | Utterberg |
| 5,575,780 A | | 11/1996 | Saito |
| 5,656,010 A | | 8/1997 | Li et al. |
| 5,716,321 A | | 2/1998 | Kerin et al. |
| 5,733,266 A | | 3/1998 | Gravlee |
| 5,772,628 A | | 6/1998 | Bacich et al. |
| 5,788,681 A | * | 8/1998 | Weaver et al. ............ 604/523 |
| 5,807,239 A | | 9/1998 | DiBernardo |
| 5,843,023 A | | 12/1998 | Cecchi |
| 5,921,956 A | | 7/1999 | Grinberg et al. |
| 5,961,444 A | | 10/1999 | Thompson |
| 5,968,022 A | | 10/1999 | Saito |
| 6,004,302 A | | 12/1999 | Brierley |
| 6,006,002 A | | 12/1999 | Motoki et al. |
| 6,010,448 A | | 1/2000 | Thompson |
| 6,027,443 A | | 2/2000 | Nag |
| 6,053,899 A | | 4/2000 | Slanda et al. |
| 6,156,566 A | | 12/2000 | Bryant |
| 6,203,533 B1 | | 3/2001 | Ouchi |
| 6,258,070 B1 | | 7/2001 | Kaldany |
| 6,273,877 B1 | * | 8/2001 | West et al. ................ 604/264 |
| 6,280,423 B1 | | 8/2001 | Davey et al. |
| 6,281,013 B1 | | 8/2001 | Grondahl |
| 6,319,192 B1 | | 11/2001 | Engel et al. |
| 6,592,547 B2 | | 7/2003 | Grimes et al. |
| 6,610,005 B1 | | 8/2003 | Tao |
| 6,623,422 B2 | | 9/2003 | Kamrava |
| 6,758,806 B2 | | 7/2004 | Kamrava et al. |
| 7,033,314 B2 | | 4/2006 | Kamrava et al. |
| 7,063,681 B1 | | 6/2006 | Peery |
| 7,201,725 B1 | | 4/2007 | Cragg et al. |
| 2004/0122286 A1 | | 6/2004 | Kamrava |

FOREIGN PATENT DOCUMENTS

| | | |
|---|---|---|
| WO | WO 97/13451 | 4/1997 |
| WO | WO-0054953 | 9/2000 |
| WO | WO-2004064903 | 8/2004 |

OTHER PUBLICATIONS

Wang, H, et al., "Decreased in vitro fertilization and cleavage rates after an equipment error during Co2 calibration," Fertility and Sterility, American Society for Reproductive Medicine, vol. 73(6), Jun. 2000, pp. 1247-1249.

Goto Y, et al., "Pregnancy achieved by transferring blastocysts into endometrial stroma in mice," Hum Reprodc, May 1992; 7(5):681-4, Department of Gynecology and Obstetrics, Faculty of Medicine, Kyoto University, Japan.

Balmaceda JP, et al., "Hysteroscopy and assisted reproductive technology," Obstet Gynecol Clin North Am, Sep. 1995; 22(3):507-18, Dept. of Obstetrics and Gynecology, University of California, Irvine, CA, USA.

Lesny, Piotr M.R.C.O.G., et al., "Transcervical embryo transfer as a risk factor for ectopic pregnancy," Fertility & Sterility, American Society of Reproductive Medicine, vol. 72(2), Aug. 1999, pp. 305-309.

Asaad M, Carver-Ward JA, "Twin pregnancy following transmyometrial-subendometrial embryo transfer for repeated implantation failure," Abstract, National Library of Medicine, Hum. Reprod., Dec. 1997, 12(12):2824-5.

Brunk, D, "Blastocyst transfer cuts multiples risk," Ob.Gyn. News, vol. 35, No. 23.

"Flexible Hysteroscopes," Contemporary OB/GYN, Apr. 15, 1999, Medical Economics, Montvale, NJ, pp. 6-11.

Napoli, LLC, PCT Search Report and Written Opinion mailed Dec. 23, 2008 for PCT/US07/005522.

Napoli, LLC, International Preliminary Report on Patentability mailed Feb. 9, 2009 for PCT/US2007/005522.

Napoli, LLC, Non-final office action mailed Dec. 30, 2002 for U.S. Appl. No. 10/080,177.

Napoli, LLC, Non-final office action mailed Nov. 3, 2003 for U.S. Appl. No. 10/080,177.

Napoli, LLC, Non-final office action mailed Jun. 27, 2006 for U.S. Appl. No. 10/080,177.

Napoli, LLC, After final office action mailed Apr. 19, 2007 for U.S. Appl. No. 10/080,177.

Napoli, LLC, Non-final office action mailed Aug. 9, 2007 for U.S. Appl. No. 10/080,177.

Napoli, LLC, After final office action mailed Jan. 28, 2008 for U.S. Appl. No. 10/080,177.

Napoli, LLC, Non-final office action mailed Jun. 26, 2008 for U.S. Appl. No. 10/080,177.

Napoli, LLC, Non-final office action mailed Apr. 19, 2007 for U.S. Appl. No. 11/388,467.

Napoli, LLC, After final office action mailed Nov. 2, 2007 for U.S. Appl. No. 11/388,467.

Napoli, LLC, Final Office Action dated Jun. 17, 2009 for U.S. Appl. No. 10/080,177.

Napoli, LLC, Final office action dated Jun. 24, 2009 for U.S. Appl. No. 11/388,467.

* cited by examiner

ENDOSCOPIC DEVICES AND METHOD OF USE

CROSS-REFERENCE TO RELATED APPLICATION

This application is a continuation-in-part of application Ser. No. 10/080,177, filed Feb. 19, 2002, which is a continuation-in-part of application Ser. No. 09/759,415, filed Jan. 12, 2001, which issued as U.S. Pat. No. 6,623,422 on Sep. 23, 2003.

BACKGROUND

1. Field

The embodiments disclosed herein relate generally to endoscopic devices, including hysteroscopes and related devices for microsurgical use.

2. Description of Related Art

Improving the success of in vitro fertilization (IVF) depends on many factors, one of which is the delivery or transfer of the embryo to the endometrial lining of the uterus and the successful implantation of the embryo therein. It is well known in the art that assisting an embryo to adhere to, or implant within, a predetermined area of the endometrial lining of the uterine wall, as opposed to simply releasing the embryo into the uterus, will enhance the success of IVF.

One method of assisted embryo transfer is found in U.S. Pat. No. 6,010,448 to Thompson in which an embryo is transferred with the aid of an endoscopic device, via a flexible catheter, to the endometrial lining and affixed thereto with an adhesive.

Another method of embryo transfer is taught in U.S. Pat. No. 5,360,389 to Chenette in which, after using pressurized $CO_2$ gas to distend the uterine walls, an endoscope is used to select an implantation site. A catheter is then used to forcibly inject the embryos into the endometrial lining.

While the embryo transfer methods of these prior art types may be generally satisfactory for their intended purposes, implantation problems can arise in which the trauma to the delicate embryos by either an injection or "adhesion" may yield less than optimal solutions and fail to achieve high IVF success rates. Accordingly, improved devices that may be useful, in one aspect, in intrauterine procedures such as IVF are desired. An improved embryo transfer method is also desired.

SUMMARY

A catheter, an endoscope (hysteroscope), and a method of introducing at least one embryo into a uterus of a subject is described. One object of the device(s) and/or method is to provide a simple gentle method for intrauterine procedures such as embryo transfer and implantation. To accomplish this gentle transfer, an improved catheter (referred alternatively and interchangeably herein as "microcatheter") with an angled tip is described. The catheter is able to work as both a microsurgical instrument, used in a method described herein to form an embryo-receiving pocket within the endometrial lining of a subject's uterus, and as the vehicle for transferring an embryo into the pocket. It has been observed that by gently securing an embryo within a pocket of endometrial lining, many of the risks of IVF, such as a tubal pregnancy, misplacement of the embryo, and loss of the embryo can be minimized. Tubal pregnancies, for example, are virtually eliminated according to this method.

Another benefit of actively implanting the embryo within the endometrial lining (the "within method") is derived from the fact that older embryos (e.g., 2 to 7 days after fertilization) may be used, thus providing for a longer period of observation which allows the most viable embryos to be selected. Higher accuracy in selecting the most viable older embryos yield the additional benefit that fewer embryos need to be implanted to assure a viable pregnancy, thereby minimizing the risk of high-order multiple births associated with those common IVF methods which place larger quantities of less mature embryos within the uterus. See, article by Doug Brunk in Ob. Gyn. News (Volume 35, number 23 at page 1-3) entitled "Blastocyst Transfer Cuts Multiples Risk".

The within method preferably uses direct visualization of the implantation area or site through an endoscopic device. To enhance the field of vision of the endoscope and to increase the maneuverability of the endoscope within the uterus, the uterine walls may be distended by pressurizing the uterus with an inert, harmless insufflation gas such as $N_2$ gas. Other gases may also work, however, the use of pure $CO_2$ gas is contraindicated because of toxicity. Gynecologic & Obstetric Investigation, Volume 43(2) at pages 73-5, 1997, entitled "Assisted implantation: direct intraendometrial embryo transfer." This article explains that the introduction of $CO_2$ gas into the uterus to distend the uterine wall and improve endoscopic viewing, (such as that claimed in U.S. Pat. No. 5,360,389), also raises the risk of acidifying the endometrial lining and therefore reduces the viability of the implanted embryo. Moreover, mixtures of $CO_2$ and atmospheric air are generally not safe because of concern over fatal air embolism.

To enhance the positioning of the catheter at the implantation site, a hysteroscope, which is an endoscopic device for intrauterine use, is used. The hysteroscope both provides direct visualization within the uterus and acts as a guide and support for the catheter.

DETAILED DESCRIPTION

Figure 1:
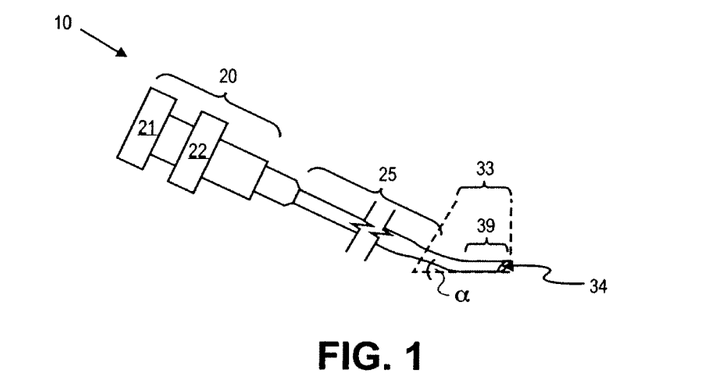
FIG. 1 is a side view of an embodiment of a catheter or microcatheter.
Figure 2:
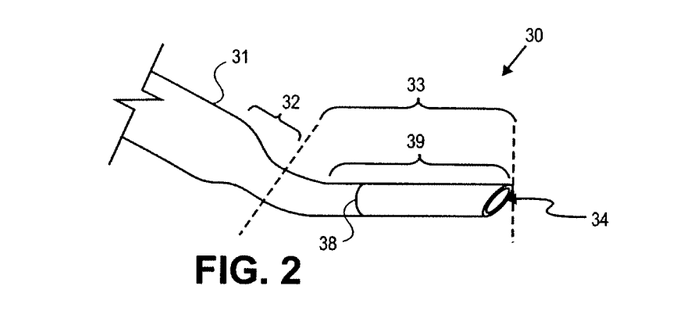
FIG. 2 is a perspective front view of the tip of the microcatheter of FIG. 1.
Figure 3:
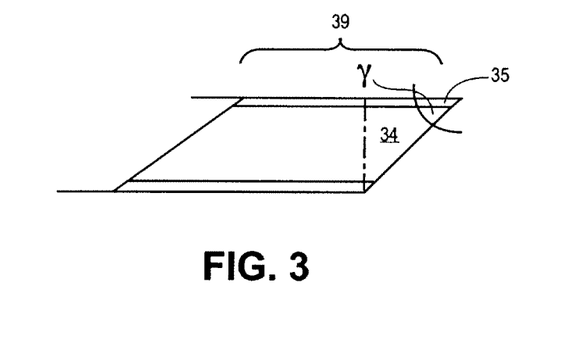
FIG. 3 is a partial cut-away side view of the tip of the microcatheter of FIG. 1.

Referring now to the drawings, illustrated in FIGS. 1-3 is one embodiment of a microcatheter. Microcatheter 10 includes, in this embodiment, operational syringe 20, with plunger 21, connected to proximal end 22 of flexible hollow shaft 25 which terminates at a distal shaped end 30. Proximal end 22 may be coupled, in one embodiment, to a leur-lock fitting.

Shaft 25 defines a lumen therethrough for, representatively, introducing one or more embryos into a uterus of a subject. In one embodiment, shaft 25 is an extruded one piece polymer material having a length on the order of 10 to 11 centimeters (cm). Suitable polymers for shaft 25 are selected such that the shaft has sufficient rigidity to be advanced through an endoscope, specifically through an endoscopic cap inserted in an endoscope (see, e.g., endoscopic cap 221 in FIG. 7) to penetrate the endometrial lining of a subject's uterus (see, e.g., FIGS. 12-14 and the accompanying text). The polymer material is also selected such that shaft 25 is flexible enough so the shaft does not penetrate the uterine muscle of the subject. One suitable polymer is polycarbonate (e.g., transparent polycarbonates). Tetrafluoroethylene (e.g., TEFLON™), polyurethane, polyethylene, and nylon materials may also be suitable. A suitable outside diameter for a proximal portion of shaft 25 is on the order of one millimeter (mm) or less. Shaft 25 includes a distal portion including shaped end 30. An external marking (e.g., marking 38) may be included at a position, for example, one centimeter (cm) from the distal end of shaft 25 to provide a visual identification of either the volume of contents within microcatheter 10 or a location of microcatheter 10, for example, in tissue.

Shaped end 30 of microcatheter 10 includes base region 31 of a similar diameter as the flexible hollow shaft 25 (e.g., 1 mm or less) and then tapers 32 over 1 to 3 mm into narrow distal end 33 which is ideally between 10 and 15 mm in length, with a representative outside diameter of 0.8 mm or less (e.g., an outside diameter less than the outside diameter of a non-tapered portion of the shaft). In one embodiment, distal end 33 has an interior diameter of approximately 10 micrometers (μm) or larger, preferably between 400 to 500 μm. Distal end 33 includes bend portion 39 such that an axis of symmetry through bend portion 39 is deflected at an angle (α) between 0 and 60 degrees, preferably 10 and 15 degrees from an axis of symmetry defined by the proximal portion of shaft 25 (in this case deflected upward as viewed). Microcatheter 10 also includes angled or beveled opening 34 angled 0 to 60 degrees (angle γ), in this case opposite the above-referenced deflection angle α. It is contemplated, however, to use angles α and γ beyond the ranges specifically recited here.

Angled opening 34 is the vehicle through which an embryo is delivered into the implantation site and may also be the microsurgical instrument used to form an implantation pocket within the endometrial lining as described with reference to FIGS. 12-15 and the accompanying text. A point at the distal end of shaft 25 representing the greatest length of shaft 25 defines tip 35. A portion of the body of shaft 25 including tip 35 may be beveled in a direction opposite bevel angle γ to yield a more refined cutting tool.

Figures 4, 5, 6:
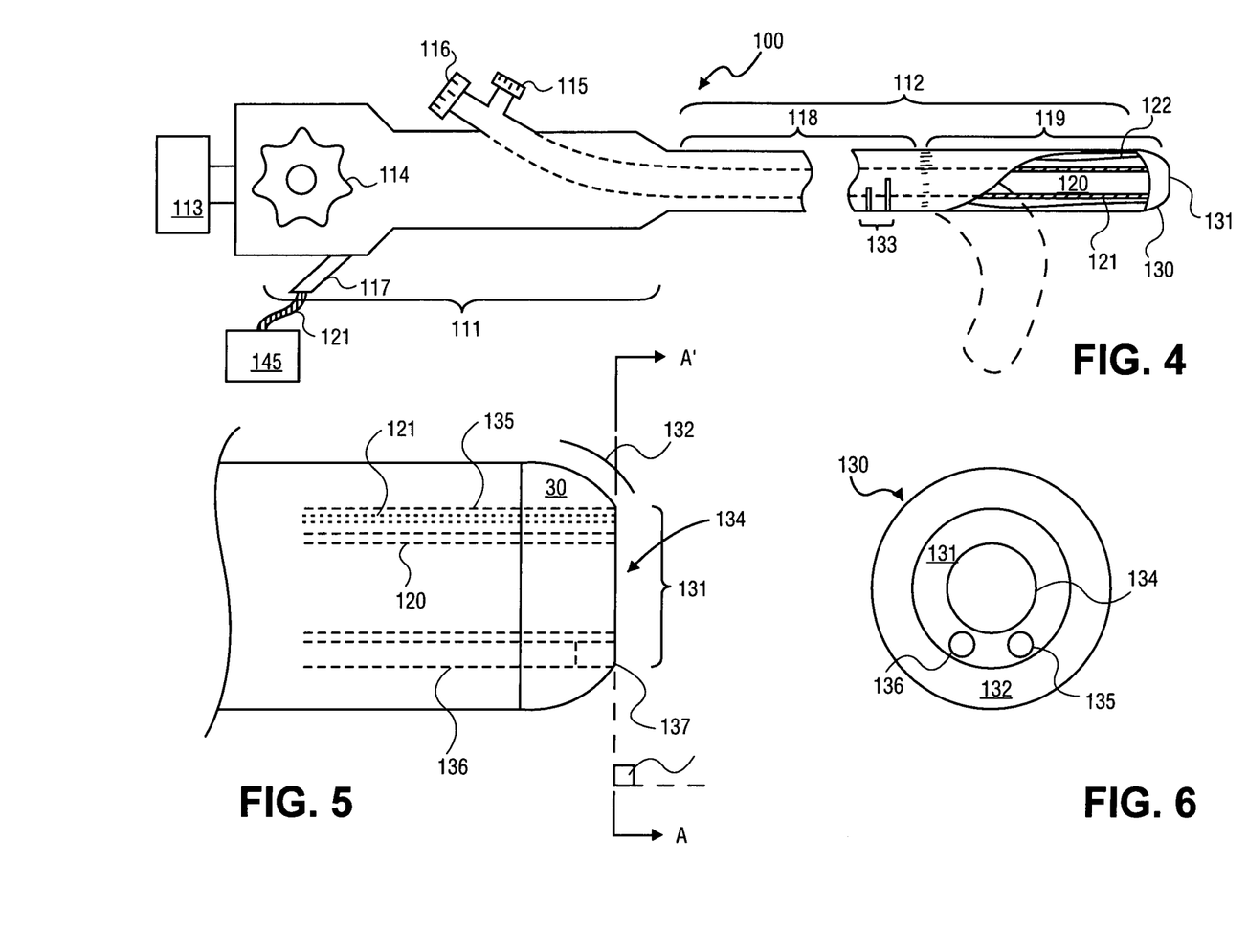
FIG. 4 is a schematic, cross-sectional side view of one embodiment of a hysteroscope.
FIG. 5 is a cross-sectional side view of a portion of the hybrid insertion arm portion of the hysteroscope of FIG. 4.
FIG. 6 is a cross-sectional view of the hysteroscope of FIG. 4 through line A-A' of FIG. 5.

Referring now to the drawings, illustrated in FIGS. 4-6 is one embodiment of a hysteroscope. Hysteroscope 100 is a two-part device, with operational section 111 at one end and hybrid insertion arm 112 at the other end. Operational section 111 is held by the operator during an intrauterine procedure, and a portion of hybrid insertion arm 112 is inserted into a subject's uterus. Supported on operational section 111 is eyepiece 113, used to visualize inside a uterus; control knob 114 used to maneuver a control structure (e.g., one or more braided wires extending to hybrid insertion arm 112 to actuate hybrid insertion arm 112 (the actuation shown in ghost lines)); and a series of access ports 115-117 extending from operational section 111 through one or more lumens inside both proximal portion 118 and distal portion 119 which form hybrid insertion arm 112. Hybrid insertion arm 112 is, in this embodiment, generally tubular and includes proximal portion 118 of a generally rigid material and distal portion 119 of a relatively flexible material (e.g., a polymer material).

The one or more lumens defined by access ports 115-117 extend through proximal portion 118 and distal portion 119 and exit or terminate at distal end 130 of distal portion 119 through guide face 131. Included among the one or more lumens is operative channel or lumen 120. Operative channel 120 extends between distal end 130 and, representatively access port 116. Operative channel 120 has a diameter suitable for insertion of a microcatheter therethrough for the purpose of performing a microsurgical procedure.

In one embodiment, distal end 130 of hybrid insertion arm 112 has edge radius 132 (e.g., a rounded edge) to facilitate gradual and gentle insertion through a subject's cervix. Edge radius provides less trauma than a blunt ended instrument and is generally able to gain entry into a smaller opening than a blunt instrument. To further aid the operator during insertion, series of locator marks 133 may be added to an exterior of hybrid insertion arm 112 to help the operator gauge the position of hybrid insertion arm 112 within a subject's uterus.

Prior art hysteroscopes with wholly flexible insertion sections are often difficult to control precisely during an intrauterine procedure. In the case of an intrauterine microsurgical procedure, hybrid insertion arm 112, having, in one embodiment, a rigid tubular proximal portion 118, preferably constructed of a smooth material such as stainless steel, seamlessly grafted/bonded to flexible tubular polymer (plastic-like) distal portion 119, is more easily maneuvered within a uterus and provides a more stable platform from which to perform the microsurgery and/or embryo implantation than from a wholly flexible hysteroscopic insertion arm.

Hybrid insertion arm 112 with both rigid proximal portion 118 and flexible distal portion 119 may be attached to a variety of hysteroscopic devices and should not be limited to being attached to, or supported by, operational section 111 detailed herein.

Often during an intrauterine procedure, uterine insufflation is desirable. Referring to FIG. 4, illustrated in hysteroscope 100 is gas port 115 which feeds into operational port 116 to operational channel 120. By sharing operational channel 120 between instruments and insufflation gas, a diameter of insertion arm 112 may be minimized yet provide the desired functions required of a hysteroscope.

Illumination within a subject's uterus may be added via illumination train extending through lumen 135 of hysteroscope 100. Lumen 135 extends, in one embodiment shown in FIGS. 4-6, between operational section 111 and hybrid insertion arm 112. Access to lumen 135 is provided by light port 117 where a light source may be coupled, preferably remotely so as not to hinder an operator's maneuvering of the device. Representatively, one or more illumination fibers 121 may extend a sufficient distance in a proximal direction from access port 117 and be coupled to light source 145 at its proximal end, so that light source 145 may remain stationary (e.g., on a table top), while hysteroscope 100 is maneuvered. In one embodiment, one or more illumination fibers 121 is inserted through lumen 135 and terminate at distal end 130. In one embodiment, one or more illumination fibers 121 include a distal end of ground glass with a blunt or, as viewed, vertical cross-section. Preferably, the distal end of one or more illumination fibers 121 aligns (is co-extensive with) distal end 130. Accordingly, in the embodiment where distal end 130 has a rounded edge, such rounded edge, in one embodiment, does not include the entire cross-section of distal end 130. Referring to FIG. 5 and FIG. 6, guide face 131 has a blunt or, as viewed, a vertical profile (β of 90°). In this embodiment, operational channel 120 and lumen 135 are disposed within a cross-section of guide face 131.

In addition to an illumination train, hysteroscope 100 includes an image train. The image train includes lumen 136 extending between operational section 111 and hybrid insertion arm 112. At the operational section end, eyepiece 113 is disposed within or coupled about lumen 316. A video camera may alternatively be coupled about lumen 136 to provide video images of the uterus. At the hybrid insertion arm end, one or more lenses 37 is/are disposed within or coupled about lumen 136. In the embodiment shown in FIGS. 4-6, lumen 136 including one or more lenses 137 is disposed within a cross-section of guide face 131. An optical fiber may be disposed within lumen 136 in between the viewing device (e.g., eyepiece 113) and one or more lenses 137.

Figure 7:
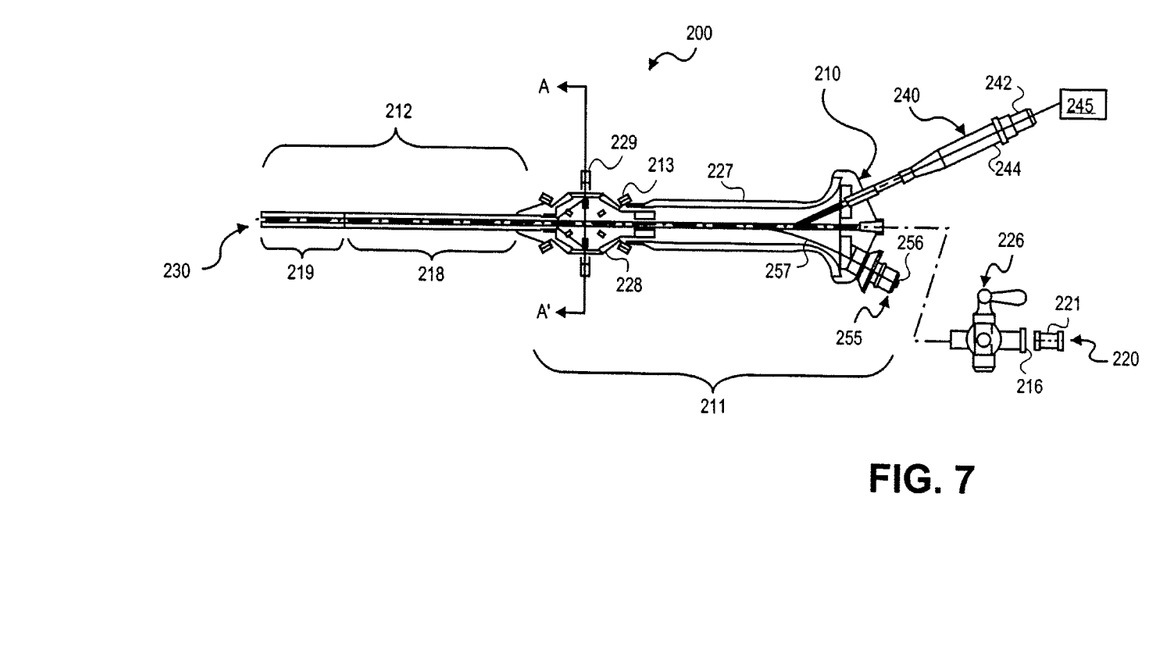
FIG. 7 is a schematic, cross-sectional side view of another embodiment of a hysteroscope.

FIG. 7 shows a schematic, cross-sectional view of another embodiment of a hysteroscope. In this embodiment, hysteroscope 200 includes operational section 211 at one end (a proximal end) and hybrid insertion arm 212 at a second end (a distal end). Hybrid insertion arm 212 is generally tubular (defining one or more lumens therethrough) and includes proximal portion 218 of a generally rigid material, such as stainless steel, and distal portion 219 of a relatively flexible material (e.g., a polymer material such as polycarbonate or polyethylene). Representatively, proximal portion 218 has a length on the order of about 8 to 19 centimeters (cm) with about an outside diameter (OD) on the order of 3 to 4 mm. Distal portion 219 has a representative length of 3 to 10 cm and a representative OD of 2.5 to 4 mm, preferably 3.0 to 3.5 mm, and preferably a representative diameter slightly smaller (at least toward distal end 230) than proximal portion 218.

Referring to FIG. 7, operational section 211 includes handle portion 227 that is preferably knurled for better holding and feel. Coupled to a distal end of handle portion 227 is lever holder 228. Disposed within lever holder 228 is articulating lever 229 that is coupled through, for example, wire members (e.g., braided wire members) to distal portion 229. Representatively, deflection of articulating lever 229 about lever holder 228 deflects distal portion 219 of hybrid insertion arm 212 to the same degree. In one embodiment, articulating lever 229 rotates about a single axis 60° in two directions (e.g., clockwise and counterclockwise) for a total range of deflection of 120°. Protruding stops 213 on lever holder 228 may be included to limit articulation of articulating lever 229.

Figure 8:
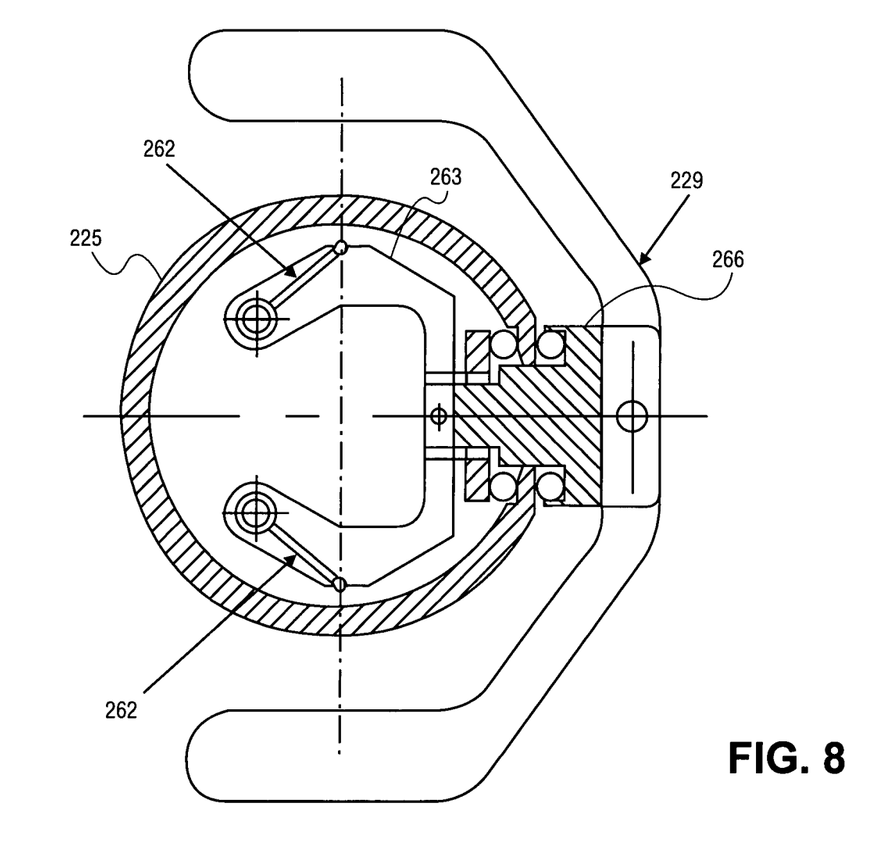
FIG. 8 is a partial cross-sectional view of the hysteroscope of FIG. 7 through line A-A'.

FIG. 8 shows a cross-section of lever holder 228 through line A-A' of FIG. 7. Lever holder 228 includes, in this embodiment, articulating lever 229 coupled to C-shaped wire mount 263 within primary lumen 225. As viewed, two wire members 262, such as braided wire members, are coupled to wire mount 263 at opposite sides thereof (e.g., 12 o'clock and 6 o'clock as viewed, respectively). Wire mount 263 is coupled to articulating lever 229 through lever holder 266.

Referring again to FIG. 7, at a proximal end of handle portion 227 of hysteroscope 200 is access port 216. Access port 216 provides access to operational channel or lumen 220. Operational channel 220 extends through the device from operational section 211 to hybrid insertion arm 212 terminating at distal tip 230. In this embodiment, access port 216 is axially aligned with operational channel 220. In one regard, the axial alignment aids the insertion of instruments such as a microcatheter into operational channel 220.

In some embodiments, a microcatheter or other instrument may be inserted in operational channel 220 through access port 216 at the same time as a gas or fluid is administered through the hysteroscope to a patient. To minimize leakage of gas or fluid around a microcatheter (e.g., microcatheter 10) or other instrument, endoscopic cap 221 is placed in access port 216. Endoscopic cap 221 of an elastic material has an opening therethrough to allow access to operational channel 220. In one procedure, endoscopic cap 221 is fitted into access port 216 and a blunt needle (e.g., an 18 gauge needle) having a lumen of a diameter suitable to allow the passing of a microcatheter or other instrument therethrough is inserted through endoscopic cap 226. The microcatheter or other instrument is then inserted through the blunt needle and advanced into operational channel 220 as desired. Once the microcatheter or other instrument is positioned, the blunt needle may be removed.

Also at a proximal end of handle portion 227 of hysteroscope 200 is a portion of illumination train 240 including illumination holder 244. A plurality of illumination fibers (e.g., glass fibers) are disposed within illumination holder 244 and join operational channel 220 within handle 227. As illustrated more clearly in FIG. 10 described below, in one embodiment, operational channel 220 and the plurality of illumination fibers are axially aligned and disposed within a primary lumen extending from operational section 211 to hybrid insertion arm 212. Light post 242 is disposed at a distal end of illumination holder 244 and may itself be a light source to the illumination fibers or be coupled to a light source. For example, light source 245 may be located remotely so as not to inhibit an operator's use of the device. At a proximal end of illumination holder 244, the illumination fibers are surrounded by tubing or sheathing and the tubing or sheathing is coupled to handle portion 227.

Still referring to FIG. 7, at a proximal end of handle 227 is a portion of image train 255 including eyepiece 256. Eyepiece 256 is coupled to lumen 236 (see FIGS. 9 and 10) which joins operational channel 220 within handle 227 and is axially aligned within a primary lumen extending from operational section 211 to hybrid insertion arm 212.

Coupled at a proximal end of operational channel 220 is valve 226 to, in one position, seal or block operational channel 220 and, in another position, to allow insufflation gas or an instrument such as a microcatheter to be passed through operational channel 220. In another embodiment, valve 226 may have three positions to, for example, provide individual access ports for an instrument and for gas or fluid (e.g., allowing introduction of a gas or fluid through operational channel 220 at the same time an instrument is inserted through operational channel 220). In one embodiment, valve 226 includes a positioning portion that may be handled by an operator to position valve 226 and that is sterilizable, removable and replaceable. A microcatheter and/or insufflation gas, in one embodiment, may alternatively be introduced to operational channel 220 at entry port 216. As illustrated in FIG. 4, a proximal end of handle 127 has, in this embodiment, a concave shape with entry port 216 at about the center axis of the end of handle 127 and illumination train 240 and image train disposed radially in alternative directions from the axis.

Figure 9:
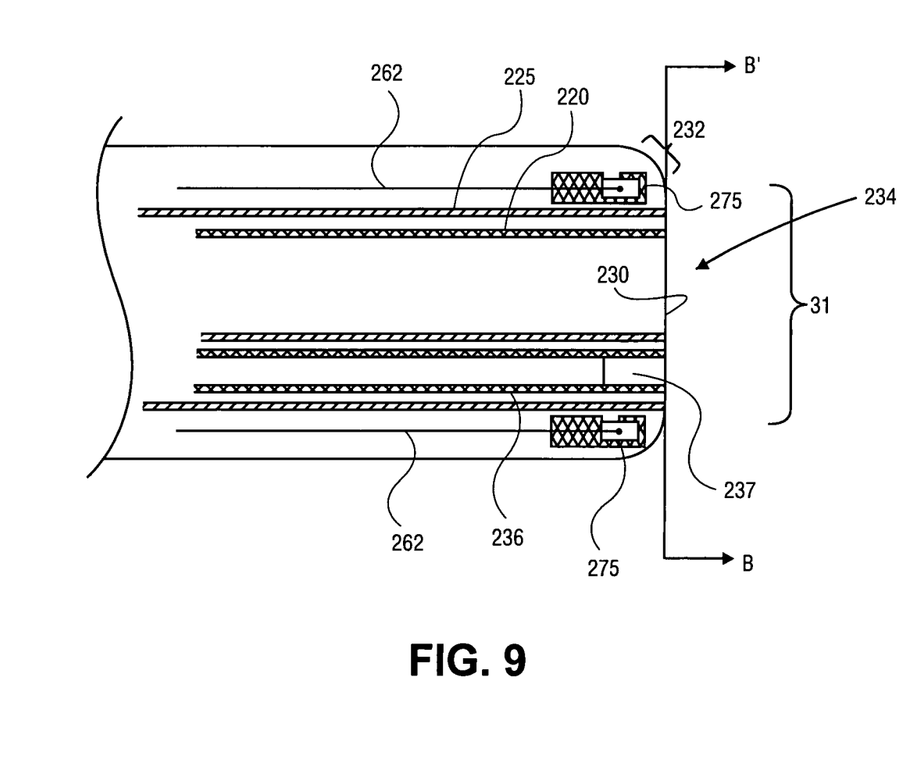
FIG. 9 is a cross-sectional side view of a portion of the hybrid insertion arm portion of the hysteroscope of FIG. 7.
Figure 10:
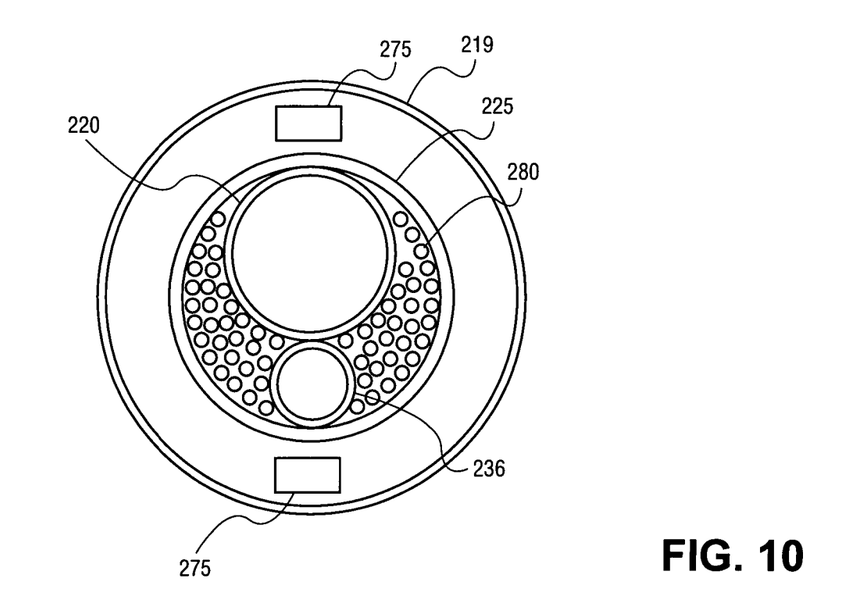
FIG. 10 is a cross-sectional view of the hysteroscope of FIG. 7 through line B-B' of FIG. 9.

FIG. 9 shows a schematic, cross-sectional side view of a distal end of hybrid insertion arm 212. FIG. 10 shows a cross-section through line B-B' of FIG. 9. Each figure shows primary channel 225 extending through hybrid insertion arm 212 to distal end 230. In one embodiment, primary channel 225 is a polymeric material of having a diameter on the order of 1.3 mm. Disposed within primary channel 225, in this embodiment, is operational channel 220 and illumination lumen 236. In a preferred embodiment, operational channel 220 has an inside diameter (ID) of about 1.5 mm or less, preferably 1.3 mm. Also disposed within primary channel 225 are a plurality of illumination fibers 280 (each having a representative diameter on the order of 0.12 mm) forming part of illumination train 240 extending back to illumination holder 244 and light post 242 and operational section 211. In this embodiment, illumination fibers 288 surround operational channel and image lumen 236. Still further disposed in operational channel 220 is image lumen 236 which forms part of image train 255 and is coupled, in one embodiment, to eyepiece 256 in operational section 211. Image fiber 257, such as a 10K or 15K image fiber commercially available from Fujikura America, Inc. of Marietta, Ga. may be disposed in image lumen 236 and coupled to eyepiece 256. At a distal end of image lumen 236 is one or more lenses 237, such as a GRIN, ILH-0.5-WD15 lens commercially available from NSG America, Inc. of Somerset, N.J.

Disposed outside of primary channel 225, preferably within a separate lumen or lumens or sheaths is co-axially disposed dumb bell 275 coupled (e.g., via adhesive) to distal end 230 of hybrid insertion arm 212. Wire members 262 are coupled to dumb bell 275 to provide for articulation of distal portion 219 of hybrid insertion arm 212 by articulating lever 229.

Referring to FIG. 9, distal end 230 of hybrid insertion arm 212 has a rounded edge 232 and a blunt (e.g., vertical) guide face 231. Accordingly, guide face 231 has a smaller diameter than the outside diameter of distal portion 219 of hybrid insertion arm 212. It is appreciated that edge 232 need not be rounded but could be linearly-sloped. Primary channel 225 is disposed within blunt guide face 231 so that illumination fibers 280 (see FIG. 7) may terminate with a blunt edge at guide face 231. Rounded edge 232 facilitates insertion into a subject.

FIGS. 11-15 show the sequential performance of an embryo implantation procedure representatively using microcatheter 10 and hysteroscope 200. The biology, timing and biochemistry involved in embryo selection and in optimizing the subject for implantation is not the topic of this invention. It is well known by those skilled in the art of how best to harvest and fertilize eggs and how best to select viable embryos. Volumes of scientific literature also exists on the hormonal, pharmaceutical and other chemical factors which should be orchestrated, monitored and taken into account when selecting the timing for embryo implantation. Accordingly, such information is omitted.

Figure 11:
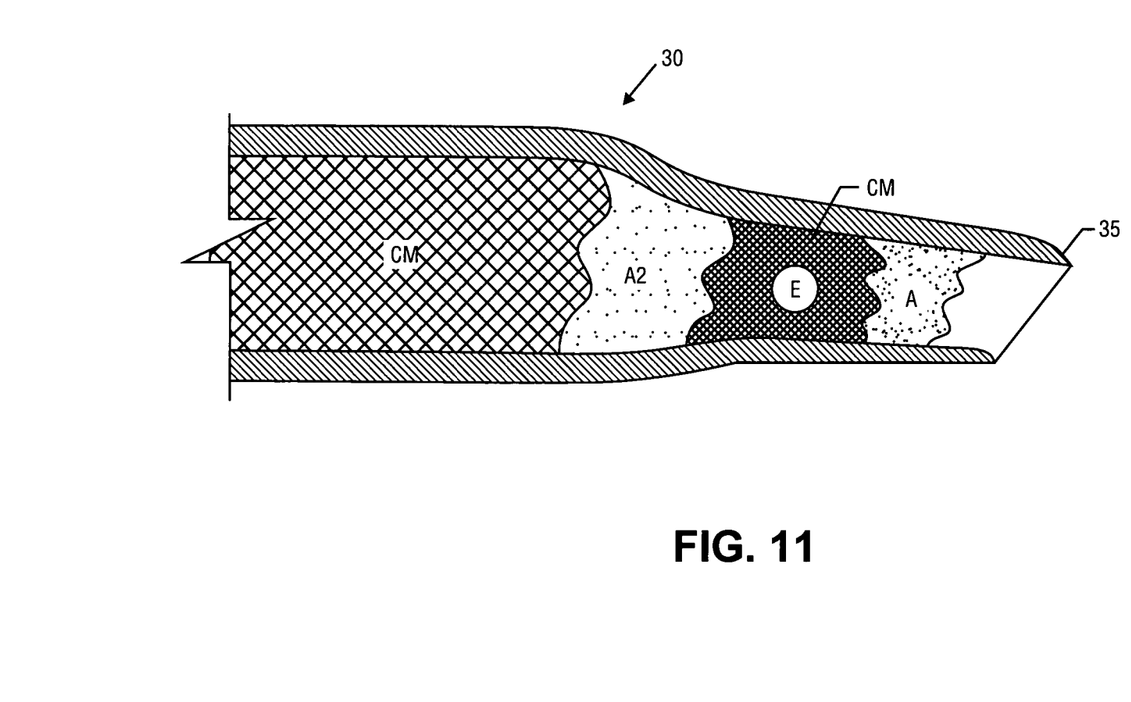
FIG. 11 is a cross-section side view of a distal end of the microcatheter of FIG. 1 containing an embryo for implantation.

Prior to any intrauterine activity, an embryo must be placed in microcatheter 10. Microcatheter 10 will be used to both prepare the site for implantation and to transfer the embryo "E" into the site. Shown in FIG. 11 is an embryo "E" immersed in a culture medium "CM" placed near distal end 33 of microcatheter 10. The culture medium "CM" serves the important role of maintaining the health and viability of the embryo "E" during the procedure. In this embodiment, the culture medium "CM" used is a "modified Human Tubal Fluid" manufactured by Irvine Scientific of Irvine, Calif. Considering the rapid pace of advancements in IVF, new and varied culture media will undoubtedly be developed or become available. Accordingly, the method described should not be limited to that culture media described herein, but rather to any suitable culture media which serves the function of maintaining embryo viability during the implantation procedure.

Prior to placing the embryo "E" into microcatheter 10, a first quantity of culture medium "CM" is drawn into microcatheter 10 and followed by a back measure of atmospheric air "A2" (e.g., 10-20 microliters (μL)). Next, the embryo "E", bathed in more culture medium "CM" (e.g., 5 -10 μL), is drawn into distal end 33 of microcatheter 10 followed by a front measure of atmosphere air "A" (e.g., 5-10 μL), thereby sandwiching the embryo "E" between a first and second measure of atmospheric air "A" and "A2". Once loaded with the embryo "E", microcatheter 10 is ready for use in the implantation procedure. Each measure of atmospheric air may be, for example, about three to twenty microliters in volume.

In one procedure, endoscopic cap 221 is inserted into access port 216 of hysteroscope 200 (see FIG. 7). A blunt needle having a lumen of a diameter suitable to allow the passing of microcatheter 10 therethrough, is inserted through endoscopic cap 221. Microcatheter 10 loaded as described above is threaded into operational channel 220 of hysteroscope 200, so that tip 35 is approximately one to two centimeters (cm) from distal end 230. The blunt needle may then be removed from the endoscopic cap so that the cap snugly surrounds microcatheter 10.

Figure 12:
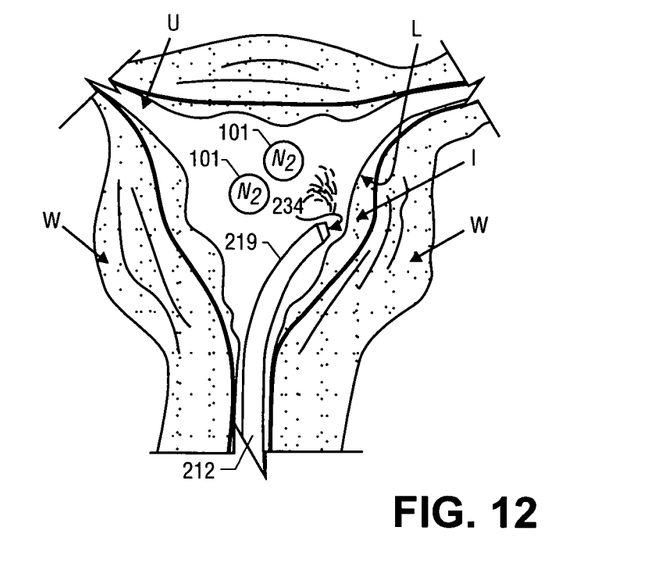
FIG. 12 is a first sequential view of an embodiment of a method of assisted embryo implantation, which shows the survey of the endometrial lining for an implantation site.
Figure 13:
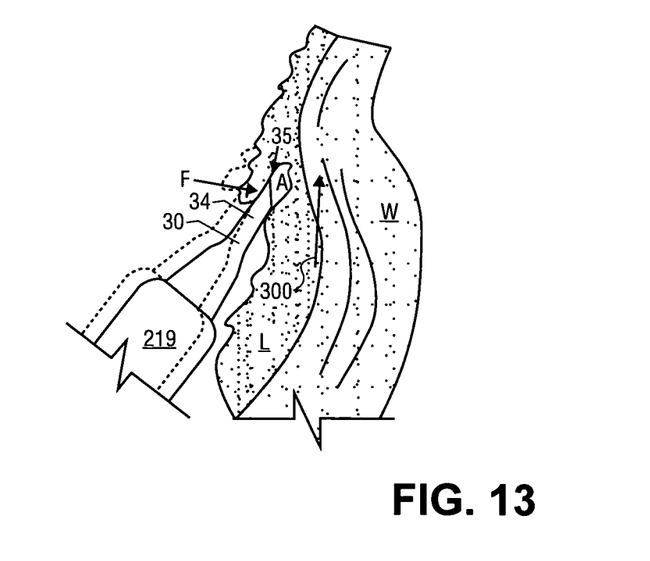
FIG. 13 is a second sequential view of the method of assisted embryo implantation, which shows the formation of an embryo-receiving pocket at the selected implantation site.

Distal portion 212 of representatively hysteroscope 200 is guided into the uterus "U" (FIG. 12). During the insertion of the hysteroscope 200, $N_2$ gas 101 is fed into the uterus "U" pressurizing or insufflating the uterus "U" and thereby distending the uterine walls "W". Depending on the needs of the operator, and the uterus of the subject, the gas 101 may be automatically maintained at a constant pressure or the operator may vary the pressure. The distension of the uterine walls "W" enhances the visualization through hysteroscope 200 within the uterus "U".

Once an embryo implantation site "I" is selected, distal end 30 of microcatheter 10 is inserted into the endometrial lining "L" (FIG. 13) and the angled opening 34 is moved generally along the path of arrow 300 making a small incision 2 to millimeters (mm) deep in the endometrial lining "L" to form a small flap "F". The front measure of atmospheric air "A" is then released from microcatheter 30 and acts to lift up the small flap "F" of the endometrial lining "L".

Figure 14:
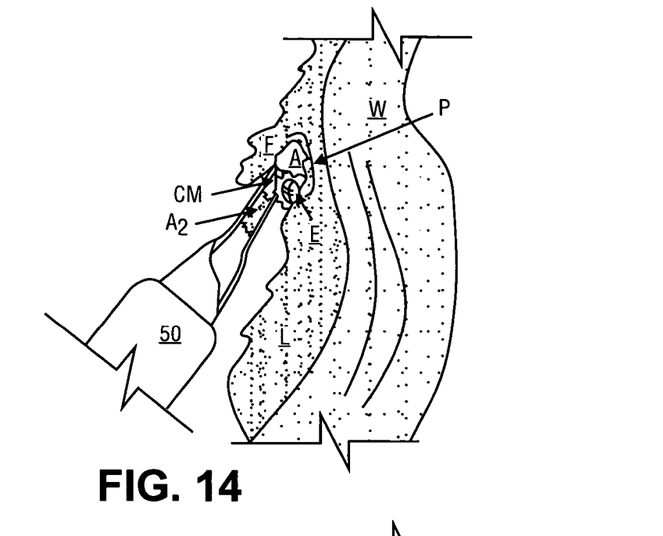
FIG. 14 is a third sequential view of the method of assisted embryo implantation, which shows the implantation of the embryo within the pocket of FIG. 13.
Figure 15:
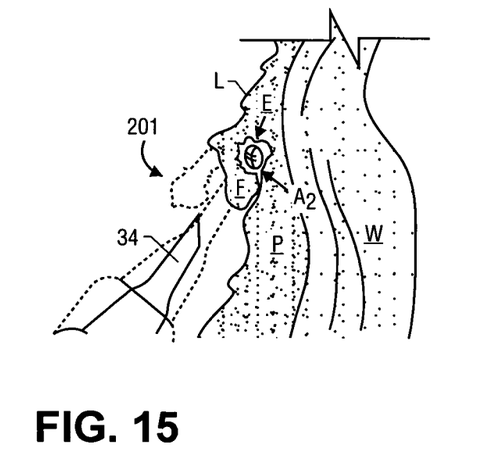
FIG. 15 is a fourth sequential view of the method of assisted embryo implantation, which shows the closure of the embryo-receiving pocket over the embryo.

Shown in FIG. 14 is the embryo-receiving pocket "P" formed beneath the small flap "F". The actual implantation of the embryo "E" into the embryo-receiving pocket "P" is performed with the same microcatheter 30 used to form the embryo-receiving pocket "P" and is accomplished by depressing plunger 21 of syringe 20 (see FIG. 1) to gently urge the embryo "E" and the back measure of atmospheric air "A2" out of microcatheter 30 and into embryo-receiving pocket "P".

The back measure atmospheric air "A2" forms a cushion around the embryo "E" which helps to protect it when the microcatheter is removed (FIG. 15) and the small flap "F" drops back into place over the embryo "E" along the line of arrow 201. To complete the procedure, hysteroscope 200 is then gently removed from the subject and post-IVF precautions and protocols should be used. Another possible advantage of a successful implantation of the embryo "E" within the endometrial lining "L" is that the length of the post-IVF precautions may be reduced.

Dependent on the subject, the number of viable embryos available and the aperture, up to two embryos may be implanted into a single pocket "P". In the case of embryo implantations into multiple pockets, additional embryos, each bathed in culture medium, are sandwiched between a measure of atmospheric air within the microcatheters and implanted into separately formed pockets "P".

Certain presently preferred embodiments of apparatus and methods for practicing the invention have been described herein in some detail and some potential modifications and additions have been suggested. Other modifications, improvements and additions not described in this document may also be made without departing from the principles of the invention. For example, the microcatheter (e.g., microcatheter 10) and hysteroscope (e.g., hysteroscope 200) have been described with reference to an IVF procedure. It is appreciated that such devices need not be specified together and either may have other uses beyond IVF procedures. Representatively, the hysteroscope may be used in connection with other devices such as biopsy forceps or other procedures such as irrigation/aspiration. The microcatheter and hysteroscope (end) are also contemplated in other than intrauterine procedures. One non-limiting example would be gastroenterological procedures.

I claim:

1. A catheter comprising:
a shaft comprising a body with a proximal portion and a distal portion, the body having a length configured for placement through an endoscopic device in an assisted embryo transfer procedure and the body defining an opening from the proximal portion to the distal portion, the distal portion having an exterior dimension suitable for insertion into a body of a subject as a procedural instrument for transferring an embryo, the distal portion having an end that is beveled in a first direction across the opening, such that a length of the shaft to a first point on the end is a first length and a length of the shaft to a second point on the end is a second length longer than the first length, a portion of the shaft including the second point is beveled in a second direction opposite the first direction defining a tip shaped to be inserted into an endometrial lining of the subject, and wherein the tip comprises a material that has sufficient rigidity to penetrate the endometrial lining of the subject and sufficient flexibility to resist penetration of a uterine muscle of the subject.

2. The catheter of claim 1, wherein the beveled end defines an angle of up to 60 degrees between the end of the distal portion and the open front end.

3. The catheter of claim 2, wherein the beveled end defines an angle of 10 to 15 degrees between the end of the distal portion and the open front end.

4. The catheter of claim 1, further comprising a tapered region approximately 1.5 centimeters from the tip and wherein an outside diameter of the shaft tapers to a greater outside diameter in the tapered region.

5. The catheter of claim 1, wherein the shaft defines a first axis through the opening therethrough and a portion of the distal portion defines a second different axis through the opening therethrough.

6. The catheter of claim 5, wherein the second axis differs by a deflection angle up to 60 degrees from the first axis.

7. The catheter of claim 6, wherein the deflection angle is in a direction opposite the first direction.

8. The catheter of claim 5, wherein the second axis differs by a deflection angle of 10 to 15 degrees from the first axis.

9. The catheter of claim 1, wherein an inner diameter of the opening at the end is at least approximately 10 micrometers in size.

10. The catheter of claim 9, wherein the inner diameter of the opening at the end is between approximately 400 and 500 micrometers.

11. The catheter of claim 1, wherein the distal portion is pointed.

12. The catheter of claim 1, wherein the tip is pointed.

13. The catheter of claim 1, wherein the tip comprises a cutting tool.

14. The catheter of claim 1, wherein the distal portion comprises a microsurgical instrument capable of being inserted into the endometrial lining.

15. An apparatus comprising:
a catheter body with a proximal portion and a distal portion and having a length configured for placement through an endoscopic device in an assisted embryo transfer procedure, the distal portion having an angled tip and an outside diameter suitable for insertion into a body of a subject as a procedural instrument, wherein the angled tip has a shape that is suitable for insertion into an endometrial lining of the subject and comprises a material that has sufficient rigidity to penetrate the endometrial lining of the subject and sufficient flexibility to resist penetration of a uterine muscle of the subject;
the distal portion of the catheter body having an end beveled in a first direction across an end opening and a portion beveled in a second direction opposite the first direction defining the angled tip; and
a portion of the distal portion having a fixed axis different than an axis of the proximal portion.

16. The apparatus of claim 15, further comprising a tapered region approximately 1.5 centimeters from the tip and an outside diameter of the shaft in the tapered region is less than an outside diameter of the shaft at a portion outside of the tapered region.

17. The apparatus of claim 15, wherein an inner diameter of the tip is at least approximately 10 micrometers in size.

18. The apparatus of claim 1, wherein the inner diameter of the tip is between approximately 400 and 500 micrometers.

19. The apparatus of claim 15, wherein the fixed axis of the distal portion differs by a deflection angle of up to 60 degrees from the axis of the proximal portion.

20. The apparatus of claim 15, wherein the fixed axis of the distal portion differs by a deflection angle of 10 to 15 degrees from the axis of the proximal portion.

21. The apparatus of claim 15, wherein the beveled end defines an angle of up to 60 degrees between the end of the distal portion and the open front end.

22. The apparatus of claim 21, wherein the beveled end defines an angle of 10 to 15 degrees between the end of the distal portion and the open front end.

23. The apparatus of claim 15, wherein the tip is pointed.

24. The apparatus of claim 15, wherein the tip comprises a cutting tool capable of being inserted into the endometrial lining.

25. An apparatus comprising:
a catheter body having a proximal portion and a distal portion and an opening from the proximal portion to the distal portion, wherein the distal portion has an outside diameter suitable for insertion into a uterus; and
a microsurgical instrument at the distal portion, the microsurgical instrument including an end of the distal portion that is beveled across the opening to form an angled tip, the angled tip shaped for insertion into an endometrial lining.

\* \* \* \* \*